United States Patent
Belluzzi et al.

(10) Patent No.: US 8,127,761 B2
(45) Date of Patent: Mar. 6, 2012

(54) DEVICE FOR DETECTING RELATIVE HUMIDITY IN A RESPIRATORY CIRCUIT

(75) Inventors: Camillo Belluzzi, Sustinente (IT); Sarah Gallini, Finale Emilia (IT); Massimiliano Solci, Correggio (IT)

(73) Assignee: Covidien AG, Neuhausen am Rheinfall (CH)

( * ) Notice: Subject to any disclaimer, the term of this patent is extended or adjusted under 35 U.S.C. 154(b) by 712 days.

(21) Appl. No.: 12/273,699

(22) Filed: Nov. 19, 2008

(65) Prior Publication Data

US 2009/0205659 A1  Aug. 20, 2009

(30) Foreign Application Priority Data

Feb. 18, 2008 (EP) .................................. 08425099

(51) Int. Cl.
*A62B 18/08* (2006.01)
*A62B 9/00* (2006.01)
*A62B 27/00* (2006.01)
*A62B 7/10* (2006.01)
*A62B 23/02* (2006.01)
*A61M 16/00* (2006.01)
*G08B 3/00* (2006.01)
*G08B 5/00* (2006.01)
*G01N 5/02* (2006.01)
*G01N 25/56* (2006.01)
*G01N 29/02* (2006.01)
*G01N 7/00* (2006.01)

(52) U.S. Cl. ......... 128/202.22; 128/201.13; 128/205.27; 73/73; 73/29.01; 73/29.04

(58) Field of Classification Search ............. 128/200.24, 128/201.13, 201.25, 202.22, 205.27–205.29, 128/204.27; 73/29.01–29.02, 29.04, 73–77, 73/335.01, 29.05; 96/4, 117; 165/223–229; 261/129; 116/206–207; 95/52; A62B 7/10, A62B 9/00, 18/08, 23/02, 27/00; A61M 16/00; G08B 3/00, 5/00; G01N 5/02, 7/00, 25/56, G01N 29/02

See application file for complete search history.

(56) References Cited

U.S. PATENT DOCUMENTS

| | | | | |
|---|---|---|---|---|
| 2,446,361 | A * | 8/1948 | Clibbon | 312/31.1 |
| 2,951,461 | A * | 9/1960 | Lockwood | 116/206 |
| 3,425,388 | A * | 2/1969 | West | 73/335.07 |
| 3,680,364 | A | 8/1972 | Carrier | |

(Continued)

FOREIGN PATENT DOCUMENTS

DE  20 2007 004247 U1  5/2007

(Continued)

OTHER PUBLICATIONS

European Search Report, dated Jul. 28, 2008.

*Primary Examiner* — Loan Thanh
*Assistant Examiner* — Oren Ginsberg
(74) *Attorney, Agent, or Firm* — Carter, DeLuca, Farrell & Schmidt, LLP

(57) ABSTRACT

A device for detecting the relative humidity in a respiratory circuit is provided which includes a housing closed towards the outside by a transparent element, and towards the inside by a membrane permeable to the humidified gas passing through the equipment to which the device is applied and wherein the housing includes a humidity indicator element.

13 Claims, 2 Drawing Sheets

U.S. PATENT DOCUMENTS

| | | | | |
|---|---|---|---|---|
| 3,702,755 | A | * | 11/1972 | Palmer .......................... 422/412 |
| 3,788,128 | A | * | 1/1974 | Strohecker ........................ 73/73 |
| 4,063,452 | A | * | 12/1977 | Bradshaw ........................ 73/73 |
| 4,201,080 | A | * | 5/1980 | Slepak et al. ...................... 73/73 |
| 4,805,608 | A | | 2/1989 | Eckstein et al. |
| 5,224,373 | A | | 7/1993 | Williams et al. |
| 5,834,626 | A | * | 11/1998 | De Castro et al. ............. 73/23.3 |
| 6,039,696 | A | | 3/2000 | Bell |
| 7,913,640 | B2 | * | 3/2011 | MacDonald et al. ......... 116/206 |
| 2001/0050080 | A1 | | 12/2001 | Seakins et al. |

FOREIGN PATENT DOCUMENTS

| | | |
|---|---|---|
| GB | 2 119 659 A | 11/1983 |
| GB | 2 297 914 A | 8/1996 |

* cited by examiner

DEVICE FOR DETECTING RELATIVE HUMIDITY IN A RESPIRATORY CIRCUIT

TECHNICAL FIELD

The present invention relates to a device for detecting the relative humidity in a respiratory circuit used for the ventilation of patients in Anaesthesia and Intensive Care Units. The device of the present invention can be successfully applied, for example, in a HME or HME-filtering device.

BACKGROUND

Medical equipment such as equipment for passive humidification by means of HME does not permit immediate verification of the humidifying efficiency.

The user of the medical equipment does not have intuitive means at his/her disposal to assess the values reached by the humidity value in a HME, for example.

For example, as is known, the humidification of patients under controlled ventilation in Anaesthesia and Intensive Care Units is performed by means of heat-moisture exchangers (HME), active humidifiers or combined methods.

These methods currently in use do not permit immediate visual control of the humidity level reached, apart from saturation which is indicated by drops of water. Normally, the manufacturer performs tests during product validation, on the basis of which it declares in the instruction manual the humidity released (or not returned) to the patient.

Nevertheless, the user does not have any means for personally verifying, instantly and intuitively, the correctness of said value and comparing the efficiency of the various products available.

SUMMARY

A device for detecting the relative humidity in a breathing circuit and an HME or HME-filtering equipment comprising the device is provided having: a housing closed towards the outside by a transparent element and towards the inside by a membrane permeable to the humidified gas passing through the equipment to which said device is applied; said housing having a humidity indicator element inside.

A ventilation system for intensive care units is also provided comprising at least one of the HME or HME filtering equipment.

DETAILED DESCRIPTION

Figure 1:
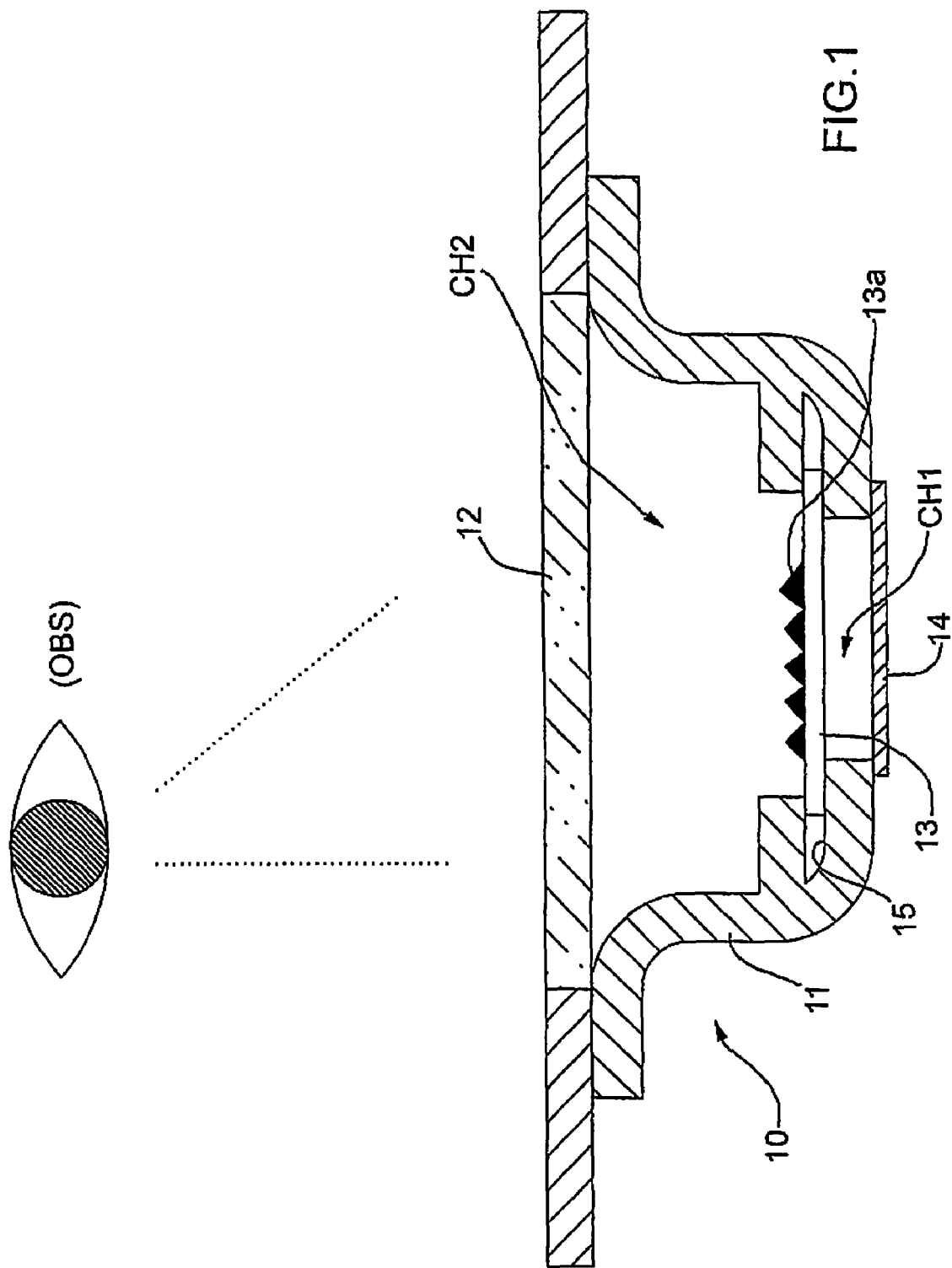
FIG. 1 is a device in accordance with the present disclosure for detecting humidity applied inside any portion of the breathing circuit used for the ventilation of patients in Anaesthesia and Intensive Care Units.

The present invention refers, therefore, to a device via which the user can immediately identify the humidifying efficiency of humidifying equipment, for example a heat-moisture exchanger (HME), an active humidifier or other combined methods, and which in general provides for display of the humidity level reached inside any medical device, in order to make the humidification conditions of the patient visible to the health operator without the use of complicated measuring instruments.

For this purpose means for indicating the humidity are used, for example humidity indicators in strips based on copper salts or cobalt salts. The copper salts have the advantage of being less toxic than the cobalt salts; said copper salts can therefore be used in medical equipment for applications normally lasting 48 hours.

In any case the present invention provides for the use of a protective barrier, for example a semi-permeable membrane such as Goretex®D, which can be crossed only by water vapour, preventing contamination of the patient by the copper or cobalt salts.

The means for display of the humidity level are inserted during the assembly phase inside the device of the present invention. In the case of a HME, for example, the detecting device is positioned inside the casing of the HME itself, in particular inside the half shell on the patient side, so that the humidity level can be displayed at the point nearest to the patient. To allow the health operator to view the indicator, the strip covered with salts must have the reactive part facing the wall of the above-mentioned half shell. A suitable housing is provided for insertion of the indicator strip on the half shell, allowing the strip to remain in position while avoiding the use of fixatives such as glue; the latter would have the drawback of covering the surface of the strip, which must remain free so that it can come into contact with the respiratory gases and consequently change colour according to the humidity content.

In the same way the device could be housed in the half shell on the ventilator side, to display the humidity level of the respiratory gases leaving the device and flowing towards the ventilator. In this position, the humidity level is lower than on the patient side, since the HME retains the moisture and the heat on the patient side. The presence of an indicator also on this side allows the confirmation to the user that the device is functioning correctly, i.e. that the patient is benefiting from an adequate level of humidification.

Applying the same principles, the device subject of the present invention for display of the humidity can be fitted inside any medical equipment, in the position where measurement of the humidity level is required, for example inside any portion of the respiratory circuit used for the ventilation of patients in Anaesthesia and Intensive Care Units.

Therefore, in the vicinity of an external wall of the equipment with humidity level to be measured, a housing must be provided to permit the fitting of a device subject of the present invention in a position such as to make a humidity indicator element visible to the user, and at the same time allow it to come into contact with the flow of respiratory gases, if necessary providing means of protection to prevent direct contact between the patient and the display means.

The present invention permits display of the humidity level reached inside any device and display of the efficiency of a humidifier device. Said invention provides the operator with means for direct display otherwise not available, permitting not only verification of the performance declared by the manufacturer but also monitoring of the patient's conditions in relation to the humidity parameter.

Figure 2:
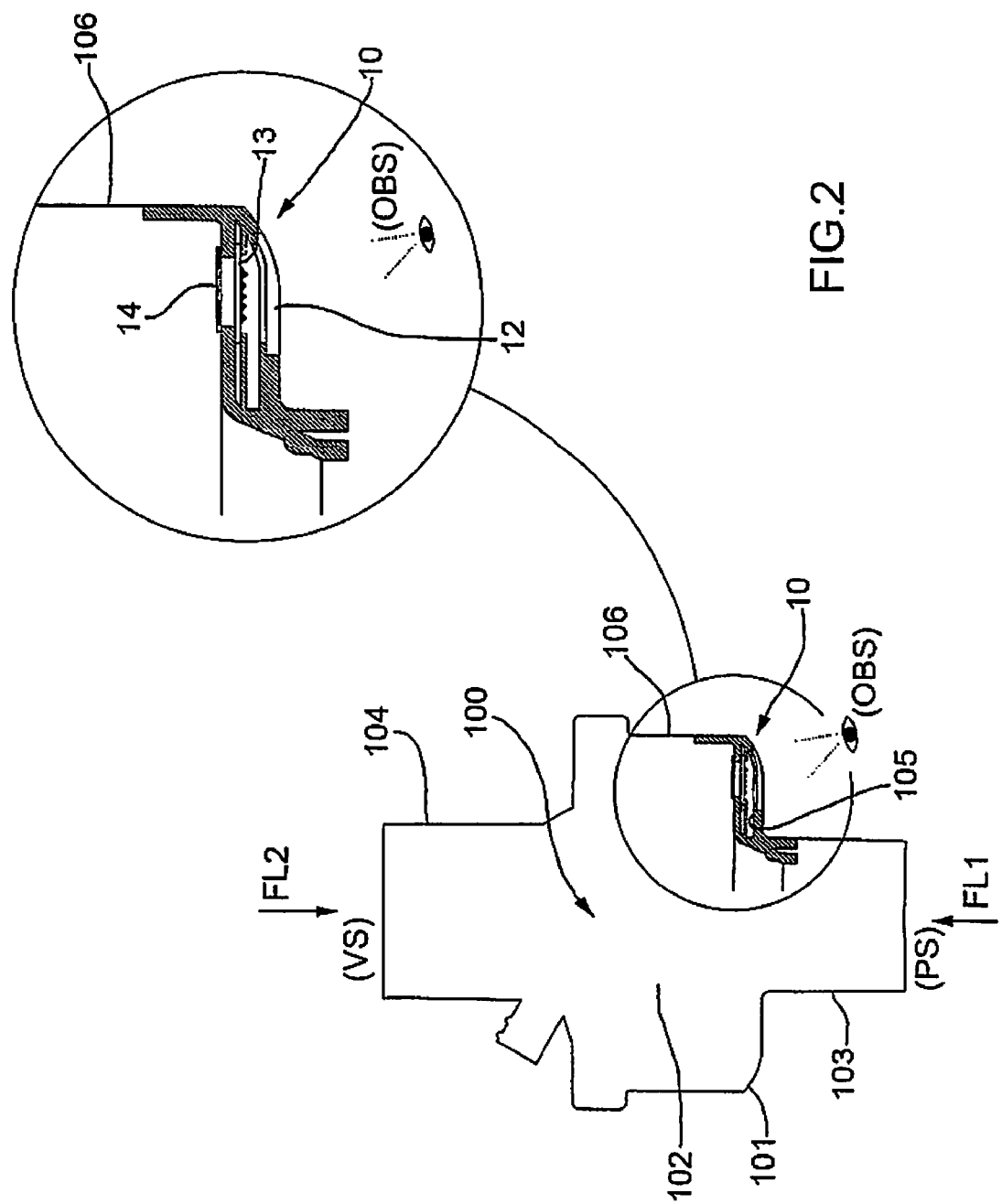
FIG. 2 is an enlarged view of a device similar to that illustrated in FIG. 1 applied to equipment comprising a HME.

The present invention will now be described with reference to the accompanying drawings, which illustrate two examples of non-limiting embodiment, in which:

FIG. 1 shows a device of the present invention for detecting humidity applied inside any portion of the breathing circuit used for the ventilation of patients in Anaesthesia and Intensive Care Units; and FIG. 2 (with a relevant enlargement) shows a device similar to the one illustrated in FIG. 1 applied to equipment comprising a HME.

In FIG. 1, 10 indicates a device for detecting humidity, used in a HME or HME-filtering equipment 100 for example (FIG. 2; see below).

With reference to FIG. 1, the device 10 comprises a housing 11 closed towards the outside by a transparent lens 12. The housing 11 is divided into two chambers CH1, CH2 by a humidity indicator element 13. More specifically, the chamber CH1 is located between said humidity indicator element 13 and a membrane 14 permeable to the humidified gas passing through the equipment (not illustrated) to which the device 10 is applied.

Advantageously, but not necessarily, the membrane 14 is made of Goretex®. In turn, the chamber CH2 is located between the humidity indicator element 13 and the lens 12 which preferably, but not necessarily, enlarges the visual information present on the element 13.

Furthermore, the humidity indicator element 13 comprises a support impregnated with at least one substance 13a that changes colour key with variation of the relative humidity level of the gas passing through. The colour change is reversible, in the sense that the particular substances 13a used in the present invention have the property of returning to their original colour once the humidity level has re-set to the value initially measured. The substance 13a that changes colour can be, for example, copper salts or cobalt salts or a mixture of the two salts.

Furthermore, the support of the humidity indicator element 13 can be permeable to the gas, for example it can be a fabric; the important thing is that each humidity level of the gas passing through is associated with a certain colour of the element 13 and that, furthermore, this colour is visible from the outside by an observer (OBS) through the lens 12.

Therefore, when the colour of the humidity indicator element 13 changes, the observer (OBS) is able to establish the humidity level of the expiration/inspiration gas passing through.

As mentioned previously, it is advisable to avoid the use of glue for fixing the humidity indicator element 13 to the housing 11 to let the whole surface free to react according to humidity level change. For this reason on housing 11 a slit arrangement 15 is provided in which the element 13 is inserted. A particular application of the device 10 of FIG. 1 is illustrated in FIG. 2.

FIG. 2 shows a HME or HUE-filtering equipment 100 which comprises, in a known manner, a central container 101 occupied in its intermediate part by a filter 102 (provided with a HME element). In turn, the central container 101 comprises two purposely shaped parts. Furthermore, the central container is connected with a patient side (PS) by means of a first duct 103, and to a ventilator side (VS) by means of at least one second duct 104.

As shown in FIG. 2, an expiration flow FL1 of a gas mixed with water vapour crosses the filter 102, in which the flow FL1 is purified of any micro organisms, and if the filter 102 is equipped with a HME element, said flow FL1 releases inside the HME particles of humidity and heat, which will be recovered during a subsequent inspiration phase, when an inspiration flow FL2 contrary to the flow FL1 will occur.

A device 10, similar to the one shown in FIG. 1, is housed in a seat 105 obtained on a wall 106 of the central container 101 on the patient side (PS). The lens 12 is positioned so as to be the continuation of the wall 106.

If the device 10 is positioned on the patient side (PS) it is useful for immediate identification of the humidifying efficiency of a humidifier device, for example a heat-moisture exchanger (HME), an active humidifier or other combined methods, and in general for display of the humidity level reached inside any medical device. In this way it is possible to verify, instantly and intuitively, the truth of the declarations made by the manufacturer in relation to the performance of the humidifying equipment, for example a heat-moisture exchanger (HME), an active humidifier or other combined methods and it allows the user to compare the efficiency of the various products available on the market.

Moreover, the device 10 could in the same way be located in the half shell on the ventilator side (VS), so as to display the humidity level of the respiratory gases leaving the HME or HME-filtering equipment 100 and flowing towards the ventilator. In this position, the humidity level is lower than on the patient side (PS), given that the HME-element retains the humidity and the heat on the patient side (PS). The presence of a device 10 also on the ventilator side (VS) serves to confirm to the user the correct functioning of the HME or HME-filtering equipment 100 during use, i.e. that the patient is benefiting from an adequate level of humidification.

Furthermore, using a device 10 on the ventilator side (VS) provides instant reliable monitoring of the possible formation of condensate which could damage the ventilator.

The main advantage of the device subject of the present invention lies in the fact that it permits immediate identification of the humidifying efficiency of humidifying equipment, for example a heat-moisture exchanger (HME), an active humidifier or other combined methods, and in general display of the humidity level reached inside any medical device, in order to make the humidification conditions of the patient visible to the health operator without the use of complicated measuring instruments.

A further advantage of the present device consists in the fact that due to a protective membrane, the particles of the salts present on the humidity indicator element do not get into the respiratory circuit of the patient.

We claim:

1. A device for detecting the relative humidity in a breathing circuit; comprising:
   a housing closed towards the outside by a transparent element and towards the inside by a membrane permeable to the humidified gas passing through an equipment to which said device is applied;
   a humidity indicator element disposed inside the housing, the humidity indicator element dividing the housing into a first chamber and a second chamber, the first chamber being located between the humidity indicator element and the membrane, the second chamber being located between the humidity indicator element and the transparent element.

2. Device, as claimed in claim 1, wherein said transparent element is a lens which enlarges the visual information present on said humidity indicator element.

3. Device, as claimed in claim 1, wherein said humidity indicator element includes a support impregnated with at least one substance that changes color with variation in the relative humidity level of the gas passing through.

4. Device, as claimed in claim 3, wherein the colour change is reversible, such that the at least one substance has the property of returning to their original color once the humidity level has re-set to a value initially detected.

5. Device, as claimed in claim 3, wherein the substance that changes color includes a salt selected from the group consisting of copper salts, cobalt salts, and mixtures thereof.

6. Device, as claimed in claim 3, wherein the support of said humidity indicator element is permeable to the gas.

7. Device, as claimed in claim 1, wherein a slit arrangement is provided on said housing in which said humidity indicator element is inserted.

8. The device according to claim 1, wherein the equipment is an HME or HME-filtering equipment.

9. The device according to claim 8, wherein the device is positioned on a patient side of the HME or HME-filtering equipment.

10. The device according to claim 8, wherein the device is positioned on a ventilator side of the HME or HME-filtering equipment.

11. The device according to claim 8, wherein the HME or HME-filtering equipment is part of a ventilation system for Intensive Care Units.

12. A heat-moisture exchanger in a respiratory circuit comprising:
   a central container having a filter therein;
   a first connector connecting the central container to a patient;
   a second connector connecting the central container to a ventilator; and
   a device housed on a wall of the central container, including:
      a housing having a first wall and a second wall, the first wall including a membrane permeable to the humidified gas passing through the heat-moisture exchanger, the second wall including a transparent element; and
      a humidity indicator element disposed in the housing and separating the housing into a first chamber and a second chamber, the first chamber being located between the humidity indicator element and the first wall, the second chamber being located between the humidity indicator element and the second wall.

13. The heat-moisture exchanger according to claim 12, wherein the transparent element is a lens which enlarges visual information present on the humidity indicator element.

* * * * *